(12) United States Patent
Kataoka

(10) Patent No.: US 6,456,054 B1
(45) Date of Patent: Sep. 24, 2002

(54) THROW-AWAY TIP WITH ABRASION SENSOR

(75) Inventor: Hideaki Kataoka, Kyoto (JP)

(73) Assignee: Kyocera Corporation, Kyoto (JP)

( * ) Notice: Subject to any disclaimer, the term of this patent is extended or adjusted under 35 U.S.C. 154(b) by 15 days.

(21) Appl. No.: 09/613,976

(22) Filed: Jul. 11, 2000

(30) Foreign Application Priority Data

Dec. 14, 1999 (JP) .......................................... 11-354835

(51) Int. Cl.$^7$ ............................................. G01N 27/00

(52) U.S. Cl. ......................................... 324/71.2; 73/104

(58) Field of Search .......................... 324/71.2; 73/104; 407/113

(56) References Cited

U.S. PATENT DOCUMENTS

| | | | | |
|---|---|---|---|---|
| 4,757,307 A | * | 7/1988 | Keramati et al. ........... | 340/680 |
| 4,818,153 A | * | 4/1989 | Strandell et al. ............ | 407/113 |
| 5,000,036 A | * | 3/1991 | Yellowley et al. ............ | 73/104 |
| 5,904,457 A | * | 5/1999 | Suwijn et al. ................ | 409/1 |

FOREIGN PATENT DOCUMENTS

| | | |
|---|---|---|
| JP | 62-88552 | 4/1987 |
| JP | 63-139641 | 6/1988 |
| JP | 3-503862 | 8/1991 |
| JP | 3-120323 | 12/1991 |
| JP | 09-038846 | 2/1997 |
| JP | 9-038846 | 2/1997 |

OTHER PUBLICATIONS

Kenneth W. Yee et al., "An On–Line Method of Determining Tool Wear by Time–Domain Analysis" Soc. of Manufacturing Engr, Dearborn, Michigan, 1982, pp 1–6.*

Hideki Aoyama, "A Study on a Throw Away Tool Equipped with a Sensor to Detect Flank Wear" Bull. Japan Soc. of Precision Engg., vol. 21, No. 3, Sep. 1987, pp 203–208.*

* cited by examiner

Primary Examiner—N. Le
Assistant Examiner—T. R. Sundaram
(74) Attorney, Agent, or Firm—Hogan & Hartson, L.L.P.

(57) ABSTRACT

For a throw-away tip provided with a sensor line of a conductive film, no technique has been established for connecting the sensor line to an external detection circuit and the like without any trouble. A throw-away tip 71 generally has an inward side face 88 and a rear side face 89 which are respectively restricted by an inward restriction face 95 and a rear restriction face 94 of a holder 92 for prevention of wobble and displacement of the throw-away tip 71 when the throw-away tip 71 is mounted in the holder 92. The inward side face 88 and the rear side face 89 are brought into abutment or intimate contact with the inward restriction face 95 and the rear restriction face 94, respectively. Therefore, the side faces (restricted faces) 88, 89 of the tip are not exposed but protected by the restriction faces 95, 94 of the holder with the tip being attached to the holder. In the light of the nature of the restricted faces, contact regions 83, 84 necessary for connection of a sensor line 82 to a detection circuit 99 and the like are provided on the side faces 88, 89 which are protected by the restriction faces 95, 94 when the tip is attached to the holder. Thus, a throw-away tip can be provided which has a configuration ensuring proper electrical connection of the sensor line. (FIG. 1)

9 Claims, 7 Drawing Sheets

THROW-AWAY TIP WITH ABRASION SENSOR

This application is based on an application No. 11-354835 filed in Japan, the content of which is incorporated herein by reference.

BACKGROUND OF THE INVENTION

1. Field of the Invention

The present invention relates to a throw-away tip for use in a cutting process.

2. Description of Related Art

Throw-away tips are known which are adapted to be attached to a holder or the like to function as a cutting tool. Such a throw-away tip is a disposable tip which is changed, rather than polished for reuse, when its cutting edge is worn out. The throw-away tip has cutting ridges provided on respective corners of a generally planar rectangular or triangular base. When one of the corner cutting ridges is worn out, another of the corner cutting ridges is used. Then, the throw-away tip is changed when all the corner cutting ridges are worn out.

However, it is not easy to check how far the cutting ridges of the throw-away tip have been worn. In view of an operating environment, it is particularly difficult to detect the abrasion degree of a cutting ridge currently used for cutting without interrupting the cutting process.

Conventional methods for detecting the abrasion degree of the cutting ridge are as follows:

(1) The cutting process is interrupted, and the throw-away tip is removed from the holder to be observed the cutting ridge by means of a tool microscope or the like.

(2) The abrasion degree of the cutting ridge is estimated by detecting a phenomenon incidental to the abrasion of the cutting ridge. For example, a reduction in cutting ability, an increase in vibration, occurrence of a noise, or the like is detected by a sensor disposed adjacent a working portion on a machine tool, and the estimation of the abrasion degree is based on a detection signal from the sensor.

In the method (1), however, the cutting process is interrupted, and the abrasion degree of the cutting ridge cannot quantitatively be determined, so that the abrasion detection cannot accurately be performed.

The method (2) requires a complicated detector, and is less reliable with a poor sensitivity for the detection of the abrasion degree.

One approach to these problems is described in Japanese Unexamined Utility Model Publication No. 3-120323 (1991). This publication discloses a throw-away tip having a sensor line of a conductive film provided along a cutting ridge on a flank thereof. It is also disclosed that the sensor line has a width conforming to an allowable abrasionwidth. In accordance with the throw-away tip disclosed in the publication, the sensor line is worn as the cutting ridge is worn, so that expiration of the life of the cutting ridge can be detected when the sensor line is cut off.

Further, Japanese Unexamined Patent Publication No. 9-38846 (1997) proposes an ordinary cutting tool (not a throw-away tip) which has a thin film circuit on a flank thereof, wherein expiration of the life of the cutting tool is automatically detected by sensing a change in electrical resistance which occurs due to abrasion of the thin film circuit as the flank is worn.

The provision of the sensor line of the conductive film along the cutting ridge on the flank for the detection of the change in the line resistance is preferred for the detection of the abrasion of the cutting ridge.

Where this approach is applied to the throw-away tip, however, it is difficult in practice to connect the sensor line provided along the cutting ridge to an external detection circuit and the like.

More specifically, the throw-away tip is a disposable tip as described above, and is very small with a size of less than 1 cm$^3$. During the cutting process, the tip in operation is exposed to a cutting fluid (water or oil) and shavings. However, no technique has been established for connecting the sensor line formed on the small throw-away tip to the external detection circuit and the like without any trouble in such a machining environment.

SUMMARY OF THE INVENTION

The present invention is to provide a throw-away tip having an abrasion sensor which serves for practical implementation to solve the aforesaid problems.

It is a principal object of the present invention to provide a throw-away tip having an abrasion sensor which, when attached to a holder or the like, ensures electrical connection between a sensor line provided thereon and an external circuit without any trouble in a cutting process.

It is another object of the invention to provide a throw-away tip which features protection of a connection portion between a sensor line provided thereon and an external circuit.

In accordance with a first inventive aspect, there is provided a throw-away tip with an abrasion sensor, which comprises: a generally planar base having a rake face defined by one surface thereof, a flank and a restricted face respectively defined by side faces thereof intersecting the rake face, the restricted face being adapted to be fixed in abutment against a restriction face of a holder when the throw-away tip is mounted in the holder; a cutting ridge defined by an intersection between the rake face and the flank; a sensor line of a conductive film provided along the cutting ridge on the flank in an electrically insulative relation with respect to the base; a contact region provided on the restricted face in an electrically insulative relation with respect to the base, the contact region being electrically connectable to an external circuit; and a connection portion provided on the base in an electrically insulative relation with respect to the base and connecting the contact region to an end of the sensor line.

In accordance with a second inventive aspect, the throw-away tip according to the first inventive aspect is characterized in that a cutting nose portion is defined by an intersection between the rake face and two adjacent flanks, wherein the sensor line extends along the cutting ridge as surrounding the nose portion, wherein the contact region includes a pair of contact regions, wherein the connection portion comprises a connection line provided on the flank to connect one of the contact regions on the restricted face to one of opposite ends of the sensor line, and a connection region provided on the rake face to connect the other contact region on the restricted surface to the other end of the sensor line.

In accordance with a third inventive aspect, the throw-away tip according to the second inventive aspect is characterized in that the base has a generally square plan shape and the restricted face includes two restricted faces defined by two side faces opposite from the respective flanks, wherein the one contact region is provided on one of the restricted faces and the other contact region is provided on the other restricted face.

In accordance with a fourth inventive aspect, the throw-away tip according to the second inventive aspect is characterized in that the base has a generally square plan shape and the restricted face includes two restricted faces defined by two side faces opposite from the respective flanks, wherein the pair of contact regions are provided in juxtaposition on one of the restricted faces.

In accordance with a fifth inventive aspect, the throw-away tip according to any of the second to fourth inventive aspects is characterized in that the nose portion includes a plurality of nose portions, wherein a plurality of sensor lines are provided for the respective nose portions, wherein a plurality of connection portions and plural pairs of contact regions connected to the respective sensor lines are provided for the respective nose portions, wherein conduction paths including the sensor lines, the connection portions and the contact regions are arranged in the same pattern.

In the first inventive aspect, the contact regions necessary for connection of the sensor line to a detection circuit and the like are provided on the restricted face which is protected by the restriction face of the holder when the tip is attached to the holder, in the light of the nature of the restricted face.

The throw-away tip generally has a restricted face which is restricted by the restriction face of the holder for prevention of wobble and displacement of the throw-away tip when the throw-away tip is attached to the holder. The restricted face is brought into abutment or intimate contact with the restriction face of the holder.

Therefore, the restricted face is not exposed to the outside but protected by the restriction face with the tip being attached to the holder.

The contact region is provided on the restricted face which, as described above, is not exposed to the outside but protected with the throw-away tip being attached to the holder. If a probe which is electrically connectable to the contact region is provided on the restriction face of the holder, the contact region and the probe are properly connected to each other in an unexposed state.

Therefore, the connection between the contact region and the probe is properly maintained during a cutting process with theuse of the throw-away tip, whereby a change in the resistance of the sensor line can constantly and accurately be detected.

In the second inventive aspect, one of the connection portions is provided on the rake face, so that the electrical conduction path can properly be provided.

In the fifth inventive aspect, the throw-away tip includes the plurality of cutting nose portions, and the plurality of sensor lines are provided for the respective nose portions, whereby the connection portions connected to the sensor lines can be arranged in a smaller space.

Where the base has a generally square plan shape, the flanks are generally defined by two adjacent side faces, and the restricted faces are located opposite from the adjacent side faces. In the third inventive aspect, the one contact region is provided on the one restricted face, while the other contact region is provided on the other restricted face.

In the fourth inventive aspect, the pair of contact regions are provided in juxtaposition on one of the two restricted faces. With this arrangement, a pair of probes are provided on one of the restriction faces of the holder, so that electrical connection between the contact regions and the probes can be established with a simplified construction.

In the fifth inventive aspect, the conductive paths including the sensor lines, the connection portions and the contact regions are arranged in the same pattern. This is advantageous for facilitation of a patterning process and reduction of production costs.

Thus, the present invention provides a throw-away tip with an abrasion sensor, which serves for practical implementation.

With reference to the attached drawings, an explanation will hereinafter be given to specific embodiments of the present invention.

DESCRIPTION OF THE PREFERRED EMBODIMENTS

Figure 1:
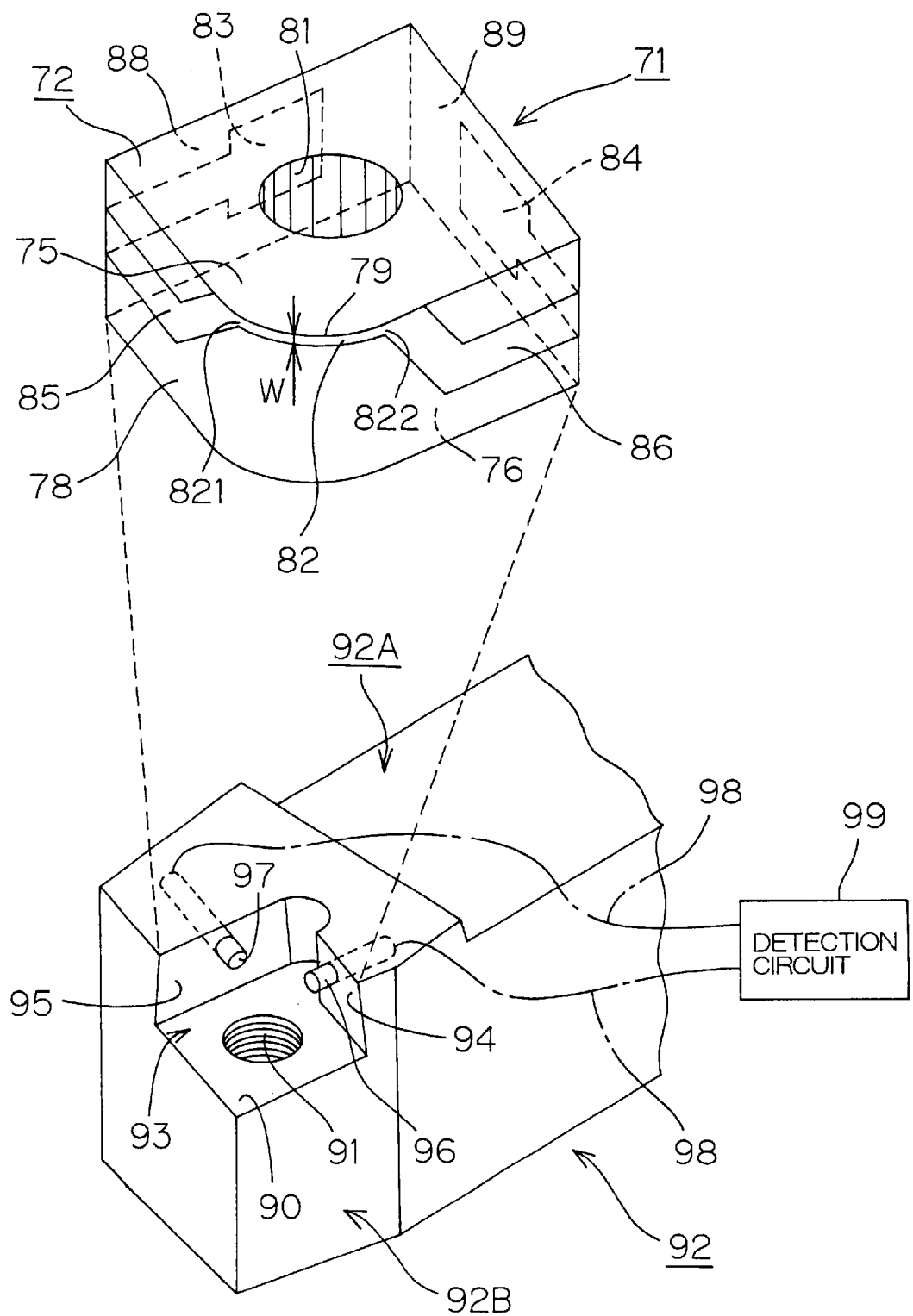
FIG. 1 is a perspective view illustrating a throw-away tip according to a first embodiment of the present invention and a holder to which the throw-away tip is attached.

FIG. 1 is a perspective view illustrating a throw-away tip 71 according to a first embodiment of the present invention and a holder 92 to which the throw-away tip 71 is attached. In FIG. 1, the throw-away tip 71 is illustrated on a greater scale for convenience of explanation.

The throw-away tip 71 has a generally planar base 72. An upper surface of the base 72 defines a rake face 75, while a lower surface of the base 72 defines a seat face 76.

The base 72 is generally rectangular in plan, and forward side faces as seen in FIG. 1 include a round face. A cutting ridge 79 is defined by an intersection between the round face and the rake face 75. The side faces define a flank 78. An inward side face 88 and a rear side face 89 of the throw-away tip 71 which are adjacent to each other define restricted faces which are to be fixed in abutment against restriction faces of a tip pocket 93 of the holder 92 when the throw-away tip 71 is attached to the tip pocket 93. The throw-away tip 71 is formed with only one cutting ridge 79. This tip is a so-called positive type, in which a cutting ridge only on the upper side is used for cutting so that the tip is not used in a vertically inverted manner. A clamp hole 81 is formed in the center of the base 72 as extending from the upper surface to the lower surface of the base.

A sensor line 82 of a conductive film is provided on the cutting ridge 79 as extending along the cutting ridge 79. The sensor line 82 is provided on the flank 78. The sensor line 82 is a conductive film line of a width W extending along the cutting ridge 79 with an upper edge thereof contacting the cutting ridge 79. The sensor line 82 is electrically insulated from the base 72. Since the throw-away tip 71 has only one cutting ridge 79 for use in cutting process, only one sensor line 82 is provided.

The width W of the sensor line 82 conforms to a reference life of the cutting ridge 79 (an allowable abrasion limit of the flank 78). The allowable abrasion limit for the reference life of the cutting ridge 79 of the throw-away tip 71 of this type is within the range of 0.05 to 0.7 mm, so that the width W of the sensor line 82 is set at a value within this range.

Where the allowable abrasion limit of the flank 78 of the throw-away tip 71 is 0.2 mm at the expiration of the life of the cutting ridge, the sensor line 82 has a width W of 0.2 mm. When the cutting process with the use of the cutting ridge 79 is in progress, the cutting ridge 79 and the flank 78 are abraded as the machining time increases. The abrasion of the flank 78 causes the sensor line 82 to be correspondingly abraded. When the abrasion width of the flank 78 exceeds the allowable abrasion limit for the reference life, the sensor line 82 having the width W conforming to the reference life is cut off by the abrasion. Since the resistance of the sensor line 82 is measured at its opposite ends by a detection circuit 99 as will be described later, the expiration of the life of the cutting ridge 79 is detected when the resistance of the sensor line 82 becomes infinite.

The holder 92 to which the throw-away tip 71 is attached includes a shank 92A attached to a tool post not shown, and a tip mounting portion 92B provided at a distal end of the shank 92A. Although the shank 92A longitudinally extends to the right in FIG. 1, an upper rear portion thereof is not shown for convenience of explanation.

The tip mounting portion 92B has the tip pocket 93 for receiving the tip. The tip pocket 93 is a recess which opens into an upper face, a front face and one side face (a forward side face in FIG. 1) of the tip mounting portion 92B. A bottom surface of the pocket 93 defines a tip seat 90 for receiving the tip 71 placed thereon. A rear face and the other side face (an inward side face in FIG. 1) of the pocket 93 serve as restriction faces 94, 95 (a rear restriction face and an inward restriction face), respectively, which are brought into abutment against the side faces of the throw-away tip 71.

Probes 96, 97 project from predetermined positions of the rear restriction face 94 and the inward restriction face 95. The probes 96, 97 are resiliently biased to project from the restriction faces 94, 95, for example, by several millimeters. The probes 96, 97 are connected to lead wires 98 provided in the holder 92 as indicated by one-dot-and-dash lines, and the lead wires 98 are connected to the resistance detection circuit 99 such as an ohm meter provided outside the holder 92.

Contact regions 83 and 84 are provided on the inward side face 88 and the rear side face 89 of the base 72. The contact regions 83, 84 are provided in a pair. The contact regions 83, 84 are composed of a conductive film, and insulated from the base 72.

Connection lines 85, 86 of a conductive film are provided as a connection portion on the flank 78 of the base 72 in an insulative relation with respect to the base 72. The connection line 85 electrically connects one end 821 of the sensor line 82 to one 83 of the contact regions, while the connection line 86 electrically connects the other end 822 of the sensor line 82 to the other contact region 84. The connection lines 85 and 86 extend from the flank 8 to the inward side face 88 and the rear side face 89, respectively, on the base 72. The connection lines 85, 86 each have a width sufficiently greater than the width W of the sensor line 82 thereby to have an electrical resistance sufficiently lower than the electrical resistance of the sensor line 82. Therefore, the connection lines 85, 86 do not affect the detection of a change in the electrical resistance of the sensor line 82.

The throw-away tip 71 is accommodated in the pocket 93. A clamp screw not shown is inserted into the clamp hole 81 of the throw-away tip 71 from the upper side, and a distal end portion of the clamp screw is brought into threading engagement with a screw hole 91 formed in the center of the tip seat 90. Thus, the throw-away tip 71 is attached to the holder 92.

When the throw-away tip 71 is mounted in the pocket 93, the probe 96 is pressed rearward by the rear side face 89 of the throw-away tip 71, and the probe 97 is pressed inward by the inward side face 88, so that the distal ends of the probes 96, 97 are flush with the rear restriction face 94 and the inward restriction face 95. Thus, the distal ends of the probes 96, 97 are respectively brought into electrical contact with the contact regions 84 and 83 on the rear side face 89 and the inward side face 88 of the throw-away tip 71. Therefore, the contact regions 83, 84 can electrically be connected to the external resistance detection circuit 99, for example, provided outside the holder 92. The resistance of the sensor line 82 is measured by means of the detection circuit 99.

With the throw-away tip 71 mounted in the pocket 93, the rear side face (restricted face) 89 of the throw-away tip 71 is almost entirely brought into intimate contact with the rear restriction face 94, while the inward side face (restricted face) 88 of the throw-away tip 71 is almost entirely brought into intimate contact with the inward restriction face 95. Therefore, even if a cutting fluid (water or oil) is applied to the distal end portion of the holder 92 or slugs cut by the throw-away tip 71 are scattered around the throw-away tip 71 during the cutting process, the cutting fluid and the slugs do not intrude between the rear side face 89 and the rear restriction face 94 nor between the inward side face 88 and the inward restriction face 95 which are kept in intimate contact with each other. That is, the inward side face 88 and rear side face 89 of the throw-away tip 71 and the rear restriction face 94 and the inward restriction face 95 of the throw-away tip 71 are protected from the cutting fluid and the slugs. Therefore, the electrical connection between the probes 96, 97 respectively provided on the rear restriction face 94 and the inward restriction face 95 and the contact regions 84, 83 respectively provided on the rear side face 89 and the inward side face 88 is properly maintained.

Although the construction illustrated in FIG. 1 is such that the probes 96 and 97 are respectively provided on the rear restriction face 94 and inward restriction face 95 of the holder 92 and the contact regions 84 and 83 are respectively provided on the two restricted faces, i.e., the rear side face 89 and the inward side face 88, restricted by these two restriction faces, the contact regions 83, 84 may be provided in juxtaposition on one of the inward side face 88 and the rear side face 89, and the pair of probes 96, 97 may be provided on the corresponding one of the restriction faces opposed to the contact regions 83, 84.

Next, an explanation will be given to a throw-away tip 1 having a plurality of cutting ridges.

Figure 2A:
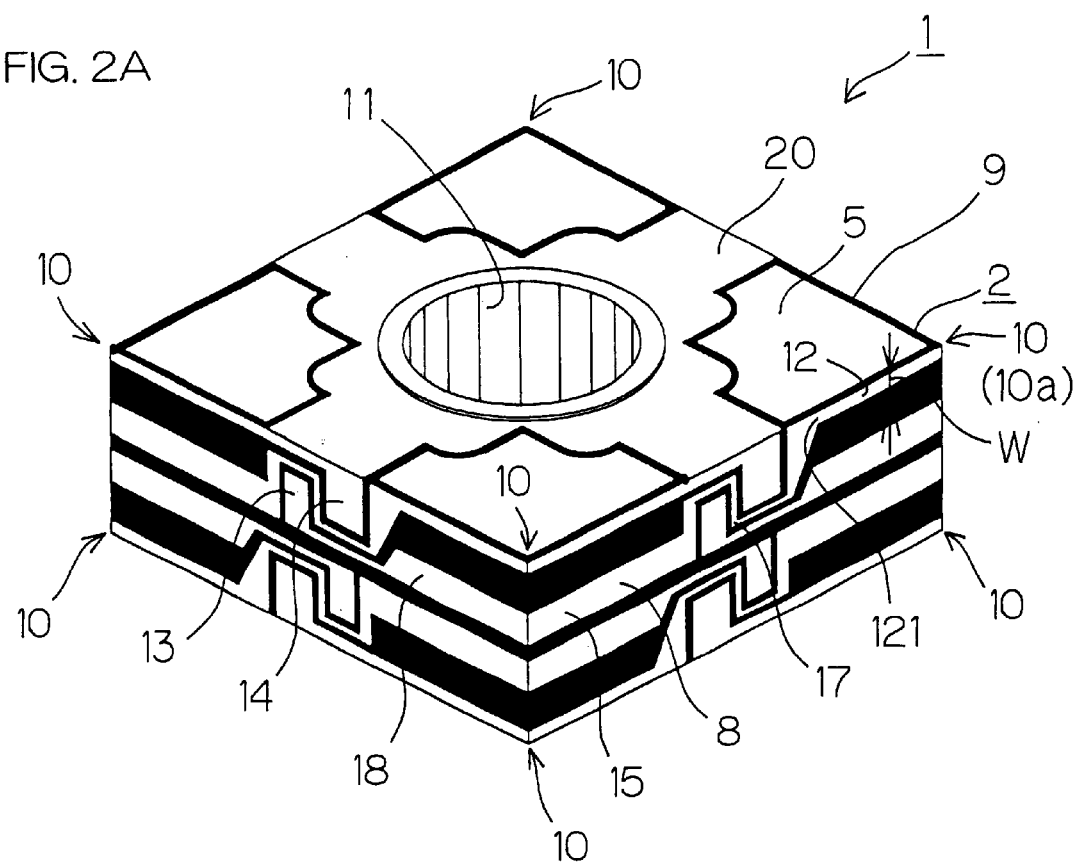
FIG. 2A is a perspective view of a throw-away tip according to a second embodiment of the invention as viewed from the upper forward side thereof.
Figure 2B:
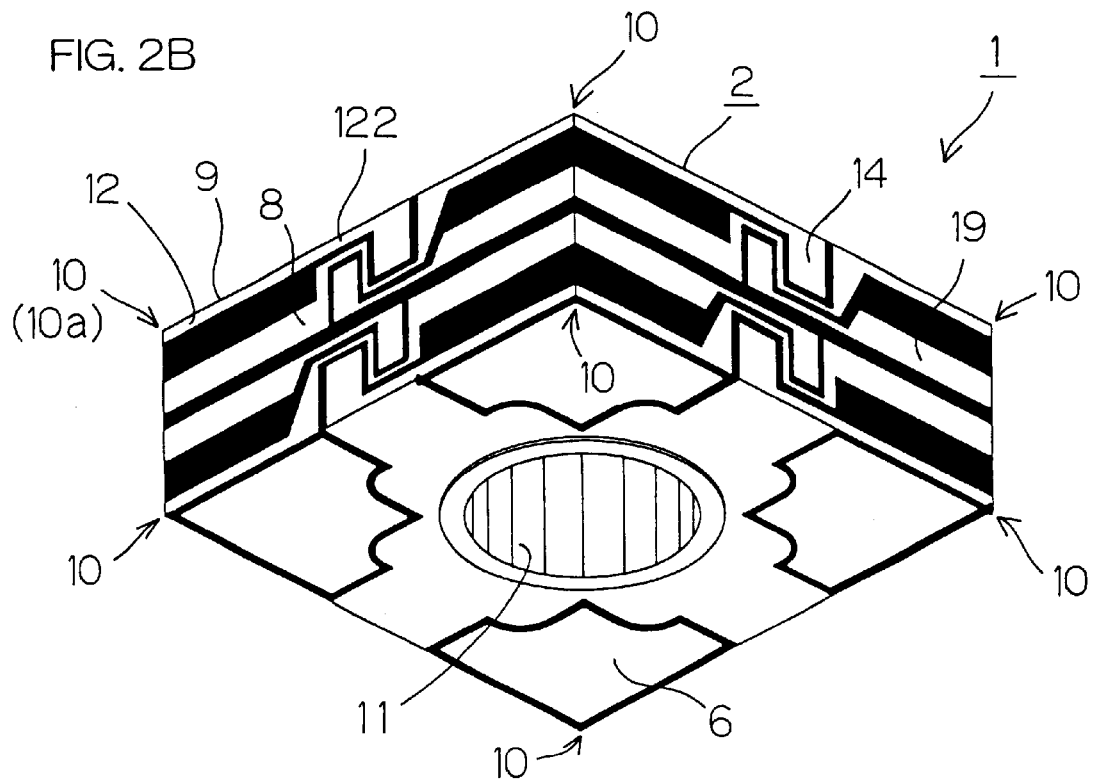
FIG. 2B is a perspective view of the throw-away tip as viewed from the lower forward side thereof.

FIG. 2A is a perspective view of the throw-away tip 1 according to a second embodiment of the present invention as viewed from the upper forward side thereof, and FIG. 2B is a perspective view of the throw-away tip 1 as viewed from the lower inward side thereof.

The throw-away tip 1 has a generally planar (rectangular column-shaped) base 2. The throw-away tip 1 is of a so-called negative type in which cutting ridges on upper and lower sides thereof are used for cutting. For convenience of explanation, one of opposite surfaces of the base 2 is called "upper surface" and the other surface is called "lower surface", though the base 2 has no distinction between the upper and lower sides thereof.

The upper surface 3 of the base 2 defines a rake face 5, and the lower surface of the base 2 defines a seat face 6. The base 2 has a generally square plan shape, and four side surfaces of the base 2 respectively define flanks 8. Intersections between the rake face 5 and the respective flanks 8 define cutting ridges 9. Further, a cutting nose portion 10 is defined by an intersection between the rake face 5 and each two adjacent flanks 8.

With the throw-away tip attached to a holder, an upper right nose portion 10a as seen in FIG. 2A, for example, is used for cutting. By turning the throw-away tip 1 by 90 degrees about a clamp hole 11 formed in the center of the base 2, another nose portion 10 can be used for cutting. By thus turning the throw-away tip 1 by 90 degrees at a time, the four nose portions 10 on the upper side can successively be used for cutting.

When the upper right nose portion 10a in FIG. 2A is used for cutting, for example, the right side surface as seen in FIG. 2A and the left side surface as seen in FIG. 2B serve as the flanks 8, and the left side face 18 as seen in FIG. 2A and the right side face 19 as seen in FIG. 2B serve as restricted faces which, with the tip 1 being attached to a tip pocket of a holder, are fixed in abutment against restriction faces of the tip pocket.

Further, by attaching the throw-away tip 1 to the holder in a vertically inverted manner, four nose portions 10 on the lower side as seen in FIGS. 2A and 2B can successively be used for cutting. When any of the nose portions 10 on the lower side is used, the upper surface serves as the seat face and the lower surface serves as the rake face. Thus, the eight nose portions 10 of the base 2 of the throw-away tip 1 can be used for cutting.

A sensor line 12 of a conductive film is provided on each of the eight nose portions 10 as extending along the cutting ridge 9. The sensor line 12 has a width W which conforms to a reference life of the nose portions 10 (an allowable abrasion limit of the flanks 8).

The side faces of the throw-away tip 1 are each divided into two portions, i.e., an upper side face portion and a lower side face portion, which are insulated from each other. Pairs of contact regions 13, 14 are provided on the respective side face portions. When the upper right nose portion 10a in FIG. 2A is used for cutting, for example, the side faces 18, 19 serve as the restricted faces as described above, and the pair of contact regions 13, 14 disposed on one of these restricted faces (as indicated by 18 in this embodiment) are electrically connectable to an external resistance detection circuit.

The pairs of contact regions 13, 14 are composed of a conductive film, and insulated from the base 2. A connection line 15 as a connection portion is provided on the base 2 in an electrically insulative relation with respect to the base 2 as extending from the side face 18 to the flanks 8. The connection line 15 extends as surrounding a nose portion 10 (on the upper forward side in FIG. 2A) adjacent to the nose portion 10a to be used. The connection line 15 electrically connects one end 121 of the sensor line 12 located on the side face 18 to one 13 of the contact regions. More specifically, the connection line 15 connected to the contact region 13 has a bent line 17 as part thereof, and the bent portion 17 is connected to the one end 121 of the sensor line 12.

The connection line 15 has a width sufficiently greater than the width W of the sensor line 12 thereby to have an electrical resistance sufficiently lower than the electrical resistance of the sensor line 12. Therefore, the connection line 15 does not affect the detection of a change in the electrical resistance of the sensor line 12.

The provision of the bent line 17 as part of the connection line 15 makes it possible to provide the connection line 15 in a parallel and spaced relation with respect to the sensor line 12 on the side walls, so that the pair of contact regions 13, 14 can advantageously be arranged in a highly area-efficient manner.

On the other hand, the other end 122 of the sensor line 12 is connected to a connection region 20 provided as a connection portion on the rake face 5. The connection region 20 is composed of a conductive film and provided in an insulative relation with respect to the base 2 to electrically connect the other end 122 of the sensor line to the other contact region 14.

Figure 3:
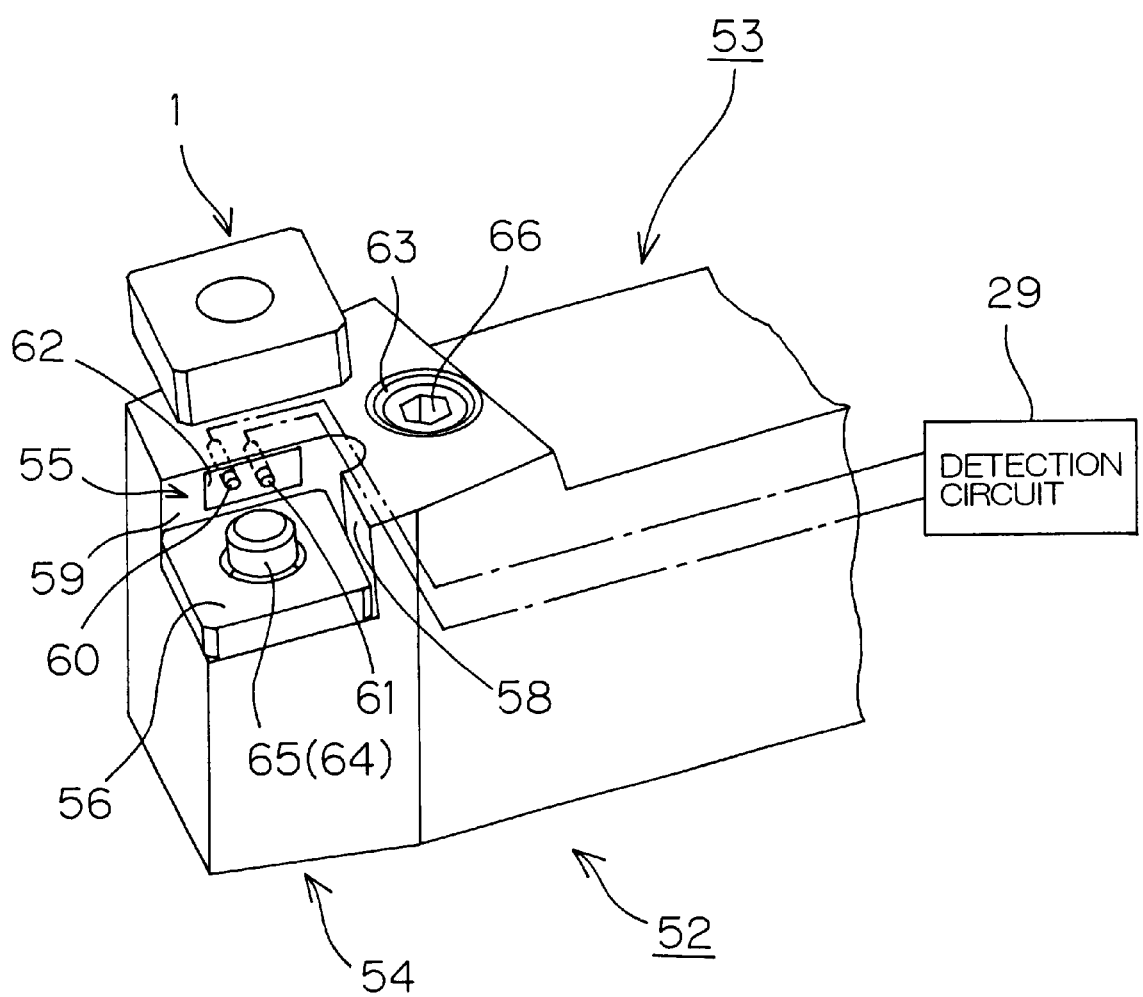
FIG. 3 is a perspective view illustrating a holder to which the throw-away tip of the second embodiment can be attached.

The throw-away tip 1 according to this embodiment is attached to a holder 52 as shown in FIG. 3 for detection of abrasion thereof.

The holder 52 includes a shank 53 to be attached to a tool post not shown, and a tip mounting portion 54 provided at a distal end of the shank 53.

The tip mounting portion 54 has a tip pocket 55 for receiving the tip. The tip pocket 55 is a recess which opens into an upper face, a front face and one side face (a forward side face in FIG. 3) of the tip mounting portion 54. A bottom surface of the pocket 55 serves as a tip seat on which the throw-away tip 1 is placed with intervention of a planar seat 56. The rear side face and the other side face (an inward side face in FIG. 3) of the pocket 55 serve as restriction faces 58, 59 (a rear restriction face and an inward restriction face), respectively, which are brought into abutment against side faces of the throw-away tip 1.

A pair of probes 60, 61 are provided in juxtaposition on the inward restriction face 59. The pair of probes 60, 61 are retained by a probe fixture 62 to be spaced a predetermined distance from each other. The probe 60 out of the pair of probes 60, 61 located on the left side in FIG. 3 is positioned at a slightly upper level than the other probe.

The probes 60, 61 are resiliently biased to project from the inward restriction face 59, for example, by several millimeters. As in the holder 92 shown in FIG. 1, the probes 60, 61 are connected to lead wires provided in the holder 52 as indicated by one-dot-and-dash lines, and the lead wires are connected to a resistance detection circuit 29 such as an ohmmeter provided outside the holder 52.

A clamp hole 63 is formed on the tip mounting portion 54 adjacent to an intersection between the rear restriction face 58 and the inward restriction face 59. The clamp hole 63 extends through the tip mounting portion 54 from an upper surface to a lower surface thereof, and an upper inner circumferential portion of the hole 63 is threaded.

The bottom (not shown) of the pocket 55 is formed with a lever groove (not shown) which has a midportion communicating with the clamp hole 63. A lever 65 which is of an L-shape in elevation and has a hollow cylindrical action portion 64 extending upward is accommodated in the groove.

By adjusting the insertion depth of a clamp screw 66 fitted in the clamp hole 63, the action portion 64 of the lever 65 is shifted between a state where the tip 1 is fixed between the rear restriction face 58 and the inward restriction face 59 and a state where the tip 1 is permitted to be removed for change. Therefore, the throw-away tip 1 can be restricted by the rear restriction face 58 and the inward restriction face 59 by screwing the clamp screw 66 into the action portion 64 of the lever 65 after the tip 1 is set.

In the second embodiment, the side face 18 (restricted face) of the throw-away tip 1 is virtually entirely kept in intimate contact with the inward restriction face 59 with the throw-away tip 1 mounted in the pocket 55. Therefore, even if a cutting fluid (water or oil) is applied to the distal end portion of the holder 52 or slugs removed by the throw-away tip 1 are scattered around the throw-away tip 1 during the cutting process, the cutting fluid and the slugs do not intrude between the side face 18 and the inward restriction face 59 which are kept in intimate contact with each other. That is, the side face 18 of the throw-away tip 1 and the inward restriction face 59 of the pocket 55 are protected from the cutting fluid and the slugs. Therefore, the electrical connection between the probes 60, 61 provided on the inward restriction face 59 and the contact regions 13, 14 provided on the side face 18 is properly maintained during the cutting process.

By turning the throw-away tip 1 by 90 degrees at a time, the four nose portions 10 on the upper side as viewed in FIG. 2A can successively be used for cutting. The 90-degree turning of the throw-away tip 1 turns the four pairs of contact regions 13, 14 by 90 degrees. Then, the contact regions 13, 14 connected to the sensor line 12 of the nose portion 10 to be used for cutting are connected to the probes 60, 61 of the detection circuit 29. Therefore, the pairs of the contact regions 13, 14 provided on the upper side face portions are arranged in the same configuration and symmetrically arranged in a 90-degree angularly spaced relation about the center of the upper surface.

Since the throw-away tip 1 can be used upside down, the pairs of contact regions 13, 14 provided on the lower side face portions are also arranged in the same configuration and symmetrically arranged in a 90-degree angularly spaced relation about the center of the lower surface.

Next, the configuration of the connection region 20 will be described.

When the electrical resistance of the sensor line 12 is measured with the contact regions 13, 14 being connected to the detection circuit 29, a predetermined voltage is applied to the one contact region 13 from the detection circuit 29, and the other contact region 14 is connected to the ground potential in the detection circuit 29. That is, either of the contact regions 13, 14 in each pair is connected to the ground potential. Therefore, the contact regions 14 in the four respective pairs provided on the four upper side face portions may electrically be connected to each other. The throw-away tip 1 employs this arrangement.

More specifically, the connection region 20 extends over the almost entire rake face 5 except portions thereof adjacent to the nose portions 10 and the clamp hole 11 to connect the contact regions 14 in the four respective pairs to the ends 122 of the four sensor lines 12.

A reason why the connection region 20 is provided on the rake face 5 is that the contact regions 13, 14 provided on the single side face 18 cannot electrically be connected to each other in the throw-away tip 1 having the contact regions 13, 14 arranged in the same configuration unless this arrangement is employed.

A reason why the connection region 20 is provided on the rake face 5 except the portions thereof adjacent to the nose portions 10 is that a portion of the rake face 5 adjacent to a nose portion 10 currently used for cutting is liable to be damaged. Therefore, it is not preferred to provide the connection region 20 adjacent the nose portions 10.

Since the contact regions 14 in the four respective pairs are electrically connected to each other, the contact regions 13 in the four respective pairs are each connected to all the contact regions 14 provided on the upper side. Therefore, the contact region 14 on the side face 19 (the other restricted face) shown in FIG. 2B may be employed as a contact region to be paired with the contact region 13 on the side face 18. In other words, the detection of the abrasion can be achieved on the two adjacent restriction faces by respectively providing the probes on the two adjacent restriction faces of the holder without the need for alteration of the configuration of the conductive film pattern of the throw-away tip 1.

Figure 4:
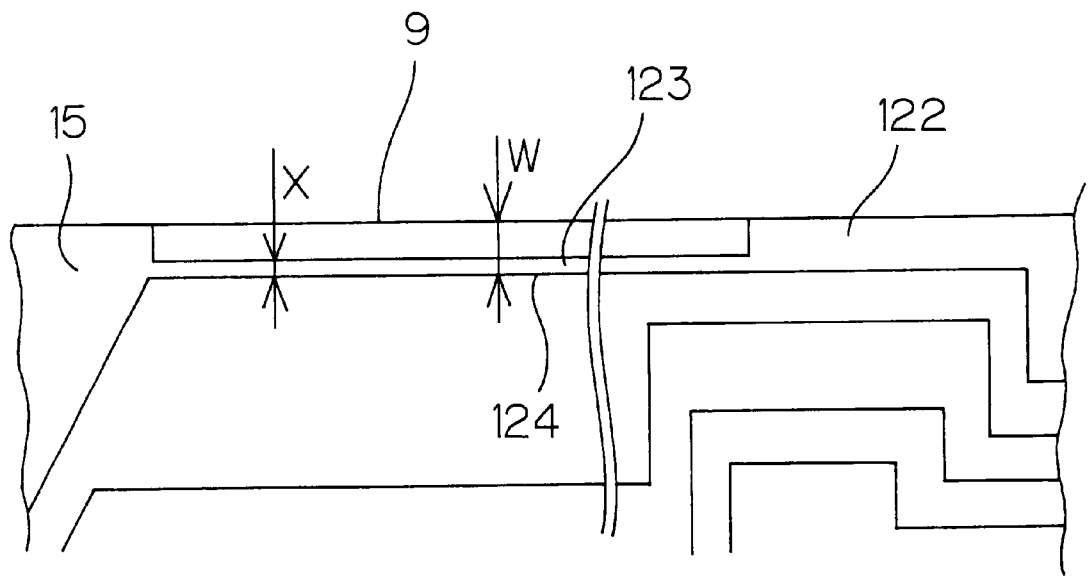
FIG. 4 is a perspective view illustrating a sensor line according to another embodiment.

FIG. 4 is a perspective view illustrating a sensor line according to another embodiment. The sensor line 12 described with reference to FIGS. 2A and 2B has the width W and extends parallel to the cutting ridge 9 as surrounding the nose portion 10 with its upper edge contacting the cutting ridge 9. On the contrary, the sensor line 123 shown in FIG. 4 has a width X (W>X) which is smaller than the width of the sensor line 12. Like the sensor line 12, the sensor line 123 is composed of a conductive film and insulated from the base 2. The sensor line 123 extends parallel to the cutting ridge 9 so that a distance between the cutting ridge 9 and a lower edge of the sensor line, i.e., an edge 124 thereof away from the cutting ridge 9, equals to a distance W.

Like the width W of the sensor line 12 shown in FIGS. 2A and 2B, the distance W conforms to the reference life of the flanks 8. The flanks 8 are abraded from the cutting ridge 9 with time in the use of the cutting ridge 9. When the abrasion reaches the sensor line 123 and exceeds the lower edge 124 thereof, the sensor line 123 is cut off by the abrasion.

The sensor line 123 may be thus configured so that the edge (lower edge) 124 thereof away from the cutting ridge 9 is spaced the predetermined distance W from the cutting ridge 9.

Figure 5:
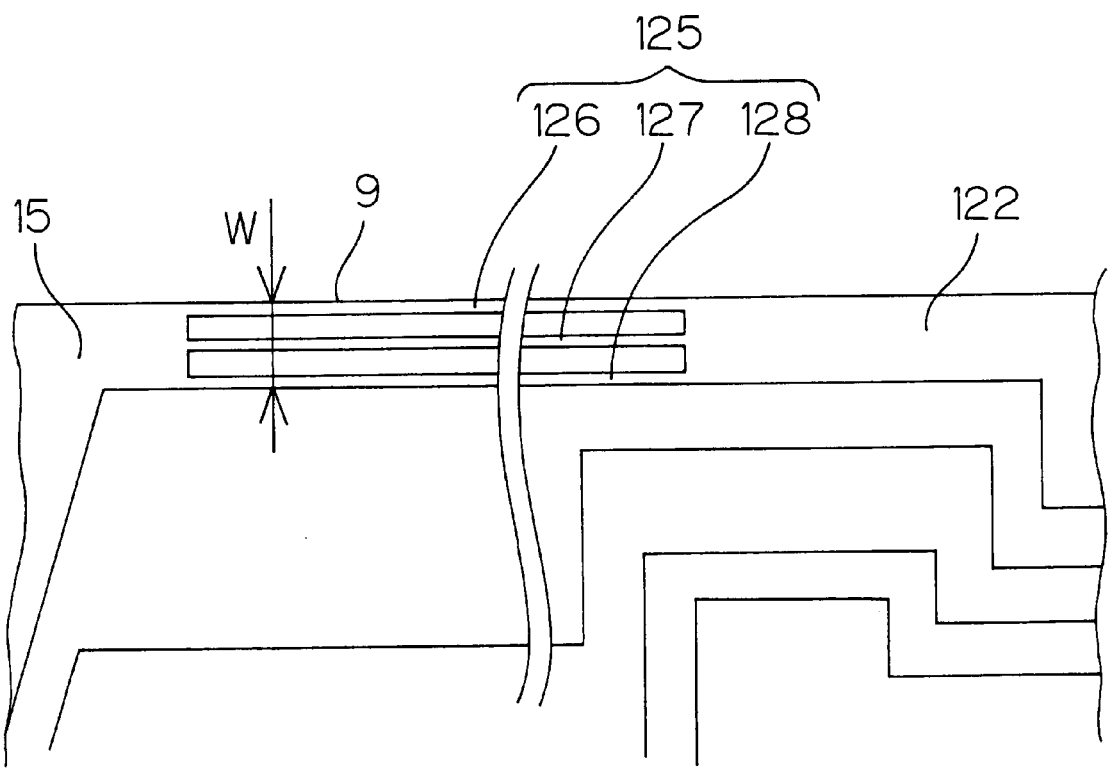
FIG 5 is a perspective view illustrating a sensor line according to further another embodiment.

FIG. 5 is a perspective view illustrating a sensor line according to further another embodiment. The sensor line 125 shown in FIG. 5 includes a plurality of lines, e.g., three lines 126, 127, 128 extending parallel to each other. A distance between the cutting ridge 9 and a lower edge of the line 128 remotest from the cutting ridge 9 is W, which is equal to the width W of the sensor line 12 shown in FIGS. 2A and 2B.

Since the sensor line 125 is constituted by the plurality of lines 126, 127, 128 extending parallel to each other, the lines are cut off in the order of increasing distance from the cutting ridge 9 by the abrasion as the abrasion of the flanks 8 proceeds. Therefore, how far the cutting ridge 9 on the nose portion 10 currently used for cutting is abraded can be detected stepwise.

The foregoing explanation with reference to FIGS. 1, 2A, 2B, 4 and 5 is directed to the cases where the distance W from the cutting ridge 9 to the lower edge of the sensor line conforms to the reference life of the nose portions or the cutting ridges (or the allowable abrasion limit of the flanks 8).

However, the distance W is not necessarily equal to the allowable abrasion limit of the flanks 8, but may be a value associated with the abrasion of the flanks 8. In the case of a preliminary (rough) cutting process or a standard cutting process, for example, the allowable abrasion limit of the flanks 8 is relatively great. In the case of a finish cutting process, on the contrary, the throw-away tip has to be changed when the flanks 8 are abraded to a certain extent. To deal with this case, the distance W may be determined so as to detect an abrasion degree at which the throw-away tip is usable but not suitable for the finish cutting process.

The present invention is applicable to throw-away tips having configurations other than the configuration described with reference to FIGS. 2A and 2B (wherein the base has a generally square plan shape). Configurations of the throw-away tips to which the present invention is applicable are shown in FIGS. 6A and 6B.

Figure 6A:
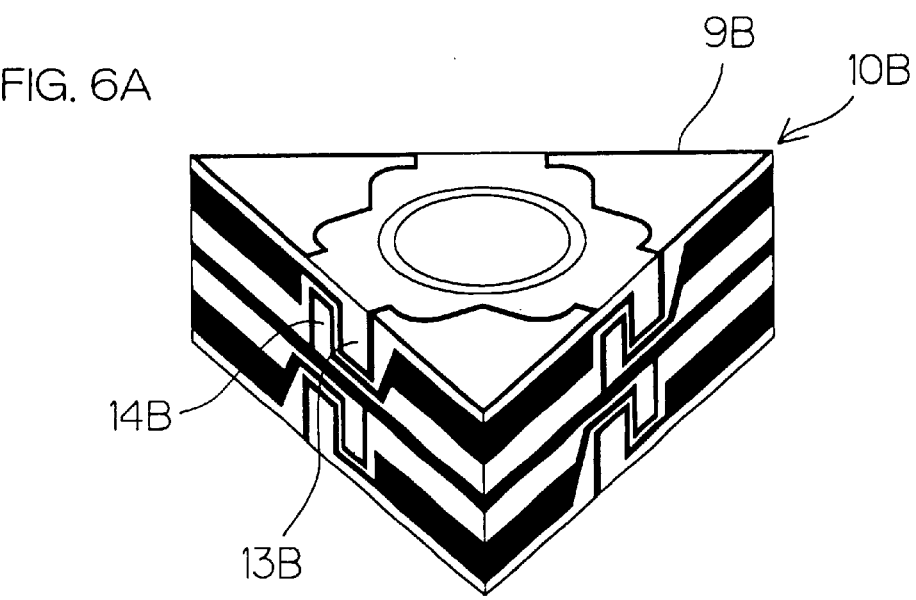
FIGS. 6A and 6B are perspective views illustrating configurations of throw-away tips to which the present invention is applicable.

FIG. 6A illustrates a throw-away tip having a base of an equilateral triangular plan shape. This tip has three nose portions on each of upper and lower sides thereof for use in cutting. That is, a total of six nose portions are provided, on which sensor lines are respectively provided. Pairs of contact regions for the respective sensor lines are provided on flanks. Where a right nose portion 10B in FIG. 6A is used for cutting, for example, a cutting ridge and contact regions associated with the nose portion 10B are denoted by reference characters 9B, 13B and 14B, respectively, in FIG. 6A.

Figure 6B:
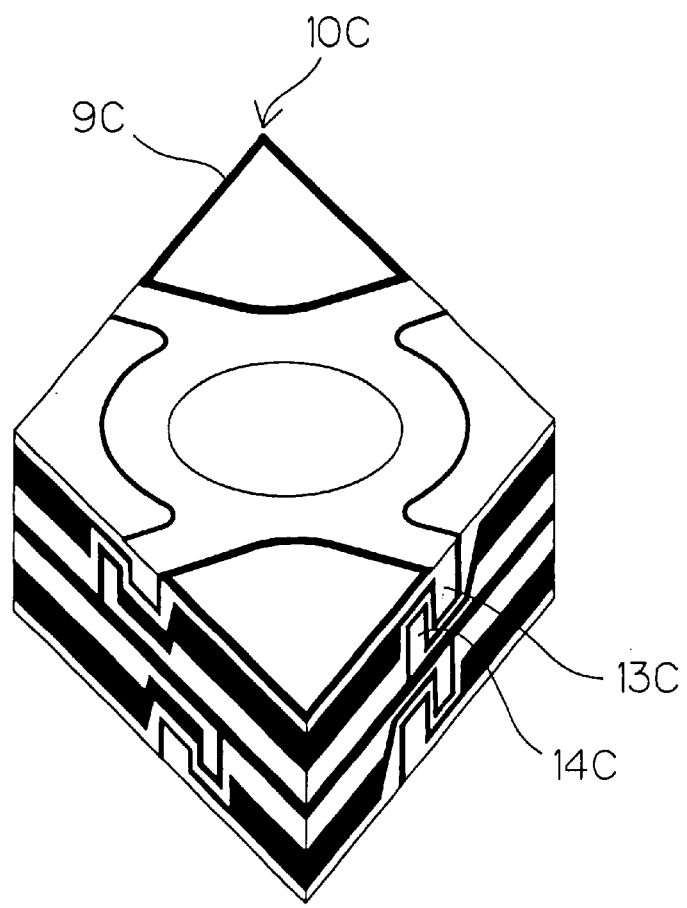

FIG. 6B illustrates a throw-away tip having a base of a rhombic plan shape. In the throw-away tip shown in FIG. 6B, two pairs of diagonally opposite acute-angle nose portions are used for cutting. Where an upper nose portion 10C in FIG. 6B is used for cutting, for example, a cutting ridge and contact regions associated with the nose portion 10C are denoted by reference characters 9C, 13C and 14C, respectively, in FIG. 6B.

Throw-away tips having the same plan shapes as in FIGS. 6A and 6B may each have a plurality of sensor lines as described with reference to FIG. 5.

Where throw-away tips having the same plan shapes as in FIGS. 6A and 6B are of a so-called positive type, upper and lower surfaces serve as a rake face and a seat face, respectively, and the throw-away tips cannot be used in a vertically inverted manner. In this case, sensor lines are provided on respective nose portions on the upper side which are usable for cutting. Further, contact regions and connection lines are provided on flanks on side faces, and a conduction region is provided on one of the rake face and the seat face.

The present invention is applicable, for example, to throw-away tips having a round or oval plan shape as well as the throw-away tips of the aforesaid configurations.

An explanation will next be given to materials and formation methods for the base, the sensor lines, the contact regions, the connection lines and the like of the throw-away tip according to the present invention.

(1) Materials for the Base

Exemplary materials for the base of the throw-away tip include sintered alumina based materials, sintered silicon nitride based material, cermets, cemented carbides, sintered cubic boron nitride (cBN) based materials and sintered polycrystalline diamond (PCD) based materials.

(2) Compositions of the Base and Preparation Methods Therefor

An explanation will hereinafter be given to preferred compositions of the base and preparation methods therefor.
① Sintered Alumina Based Material A sintered alumina based material to be herein employed consists essentially of 2 to 30 wt % of $ZrO_2$, 0.01 to 5 wt % of at least one selected from oxides of Fe, Ni and Co, the balance $Al_2O_3$ and inevitable impurities. At least one of the oxides of Fe, Ni and Co is added as a third component in a predetermined proportion to an $Al_2O_3$-$ZrO_2$ system, and the resulting mixture is highly densified by a hot isostatic sintering process, whereby the fracture toughness of the material can remarkably be improved.

The sintered alumina based material is prepared in the following manner. A powder mixture containing 10 to 20 wt % of $ZrO_2$, 0.2 to 2 wt % of at least one of the oxides of Fe, Ni and Co, the balance $Al_2O_3$ and inevitable impurities is molded into a compact, which is in turn baked at a temperature of 1400 to 1500° C. and further baked at a temperature of 1300 to 1500° C. by a hot isostatic sintering process, thereby providing a sintered material having a mechanical strength of not lower than 110 kg/mm$^2$.

As described above, at least one of the oxide of Co, Ni and Fe is present as the third component in a proportion of 0.2 to 2 wt % in the powder mixture. If the proportion is lower than 0.2 wt %, the resulting material does not have an improved fracture toughness. If the proportion is greater than 2 wt %, the resulting material has a reduced bending resistant strength.

$ZrO_2$ is preferably present in the sintered material in a proportion of 10 to 20 wt %, particularly 15 to 20 wt %. If the proportion of $ZrO_2$ is smaller than 10 wt %, a less energy is absorbed at a crack front, resulting in less improvement of the toughness. On the other hand, if the proportion of $ZrO_2$ is greater than 20 wt %, the proportion of monoclinic $ZrO_2$ (m-$ZrO_2$) in the $ZrO_2$ crystalline phase of the sintered material is increased, so that the proportion of a $ZrO_2$ portion contributory to the energy absorption at the crack front is correspondingly reduced, resulting in a reduction in the fracture toughness.

The proportion of the monoclinic $ZrO_2$ in the $ZrO_2$ crystalline phase of the sintered material is preferably not greater than 50%, particularly not greater than 30% based on the total $ZrO_2$. If the proportion of the monoclinic $ZrO_2$ is greater than 50%, the fracture toughness is remarkably reduced. Tetragonal $ZrO_2$ (t-$ZrO_2$) or cubic $ZrO_2$ (c-$ZrO_2$) is also present in the crystalline phase. When the tetragonal or cubic $ZrO_2$ is present in a proportion of not smaller than 50%, a phase transition of t-$ZrO_2$→m-$ZrO_2$ or c-$ZrO_2$→t-$ZrO_2$→m-$ZrO_2$ occurs, whereby an energy is effectively absorbed at the crack front.

In the sintered alumina based material, the $Al_2O_3$ crystals preferably have a grain diameter of not greater than 1 μm, and the $ZrO_2$ crystals preferably have a grain diameter of not greater than 1 μm, particularly not greater than 0.5 μm. If the grain diameters of these crystals are greater than these levels, the bending resistant strength is reduced.

A preparation method for the sintered alumina based material is as follows. First, 10 to 20 wt % of $ZrO_2$ and 0.2 to 2 wt % of an oxide of Co, Ni or Fe or a compound convertible to the oxide during the sintering on an oxide basis are weighed and mixed with $Al_2O_3$ having an average grain diameter of not greater than 1 μm, and then the resulting mixture is dispersed and milled in a medium including a dispersant, distilled water and the like. After the milling, the resulting paste is molded into a compact by known molding means, and then the compact is sintered.

For the sintering of the compact, the compact is baked under a normal pressure in an atmosphere, then baked at a temperature of 1400 to 1500° C. with the use of a hot press, and further baked at a temperature of 1300 to 1500° C. by a hot isostatic sintering process.
② Sintered Silicon Nitride Based Material A sintered silicon nitride based material to be herein employed consist essentially of 85 to 95 mol % of silicon nitride, 1 to 5 mol % of an element of the Group IIIa in the periodic table on an oxide basis, and 3 to 10 mol % impurity oxygen on an $SiO_2$ basis with an aluminum compound being present in a proportion of not greater than 1 wt % on an oxide ($Al_2O_3$) basis. The amount of the impurity oxygen herein means an oxygen amount determined by subtracting the amount of oxygen incorporated in oxides of the Group IIIa element in the periodic table from the total oxygen amount in the sintered material, and the impurity oxygen is mostly attributed to impurity oxygen in a starting powdery silicon nitride material and the added silicon oxide.

If the proportion of silicon nitride is smaller than 85 mol % or the proportion of the Group IIIa element in the periodic table is greater than 5 mol % on an oxide basis, the hardness of the resulting sintered material is reduced. If the proportion of silicon nitride is greater than 96 mol % or the proportion of the Group IIIa element in the periodic table is smaller than 1 mol % on an oxide basis, a highly dense compact cannot be provided, whereby the strength of the resulting sintered material is reduced. On the other hand, if the proportion of the impurity oxygen is greater than 10 mol % on a silicon oxide ($SiO_2$) basis, the toughness and chipping resistance of the resulting sintered material is reduced. If the proportion of the impurity oxygen is smaller than 3 mol %, a highly dense compact cannot be provided, whereby the strength of the resulting sintered material is reduced. If the proportion of the aluminum compound is greater than 1 wt %, the reaction resistance to cast iron is reduced, whereby the abrasion resistance of the throw-away tip is reduced during a high speed cutting process.

A preferred composition of the sintered material is such that silicon nitride is present in a proportion of 88 to 95 mol %, the Group IIIa element in the periodic table is present in a proportion of 2 to 5 mol % on an oxide basis, and the impurity oxygen is present in a proportion of 2 to 8 mol % on a silicon oxide basis. Further, the aluminum compound is preferably present in the sintered material in a proportion of not greater than 0.5 wt %, particularly not greater than 0.3 wt %, on an oxide basis.

Examples of the Group IIIa element in the periodic table includes Y, Sc, Yb, Er, Dy, Ho and Lu, among which Er, Yb and Lu are preferred.

The sintered silicon nitride based material is constituted by a silicon nitride crystalline phase and a grain boundary phase containing the Group IIIa element, silicon, nitrogen and oxygen. It is important that the silicon nitride crystalline phase has a lattice constant of not greater than 7.606 angstroms, particularly not greater than 7.602 angstroms, along the a-axis thereof and a lattice constant of not greater than 2.910 angstroms, particularly not greater than 2.908 angstroms, along the c-axis thereof. If the lattice constants along the a-axis and the c-axis are greater than 7.606 angstroms and 2.910 angstroms, respectively, the ionicity of silicon nitride is increased, thereby reducing the bonding strength of silicon nitride. Therefore, silicon nitride readily reacts with a workpiece during the cutting process, so that the so-called diffusion abrasion of the throw-away tip is increased to reduce the abrasion resistance of the throw-away tip. The silicon nitride crystalline phase is present as β-type needle crystals which have minor diameters of 0.1 to 3 μm and an average aspect ratio (major diameter/minor diameter) of 2 to 10.

The grain boundary phase may be amorphous, but is preferably crystallized. The crystalline phase is preferably constituted by apatite, YAM, wallastenite, a disilicate or a monosilicate.

An element of the Group IVa, Va or VIa in the Periodic Table such as W, Mo, Ti, Ta, Nb or V, or a carbide, nitride or silicate thereof may be present in an appropriate amount in the sintered silicon nitride based material. Further, SiC in the form of dispersible particles or whisker may be present in an appropriate amount in the sintered silicon nitride based material to form a composite material for improvement of the characteristics of the sintered silicon nitride based material.

In production of the sintered silicon nitride based material, silicon nitride powder as a starting powdery material is used as amain component. The silicon nitride powder may be either $\alpha$-$Si_3N_4$ or $\beta$-$Si_3N_4$. The silicon nitride powder preferably has a particle diameter of 0.4 to 1.2 μm.

An oxide of a Group IIIa element in the periodic table and a silicon oxide powder are used as an additive component. These components are properly weighed, and mixed together and milled in a ball mill. The proportions of these components are controlled so that the oxide of the Group IIIa element in the periodic table and silicon oxide are present in proportions of 1 to 5 mol % and 3 to 10 mol %, respectively, in a compact before the sintering, and the aluminum compound is not added to these components but is incorporated as an impurity in the compact in a proportion of not greater than 1 wt % on an oxide basis. Silicon oxide is present in the compact in an amount which is equivalent to the amount of the impurity oxygen in the silicon nitride powder on a silicon oxide basis. Therefore, the starting composition is determined in consideration of contamination with an aluminum component from the ball mill and the like during the milling and an oxygen content due to oxidation.

For preparation of a throw-away tip base, the powder mixture is molded into a compact, for example, by press molding, cast molding, extrusion molding, injection molding or cold isostatic molding. The compact is sintered, for example, by a hot press process, a normal pressure sintering process or a nitrogen gas pressure sintering process, followed by a hot isostatic sintering process (HIP) in which the resulting compact is baked under a high pressure, e.g., 2000 atm, or by immersing the compact in a frit bath or coating the compact with a glass seal and then subjecting the resulting compact to the HIP process for densification of the compact. If the sintering temperature is excessively high, diffusion of aluminum into the principal silicon nitride crystal phase is promoted to form a solid solution thereof, and the strength of the resulting sintered material is reduced due to excessive growth of grains. Further, the excessively high sintering temperature requires an expensive production apparatus. Therefore, the sintering is preferably performed at a temperature of 1650 to 2000° C., particularly, 1700 to 1950° C., in a non-oxidizing atmosphere containing nitrogen gas.

③ Cermet

For preparation of the cermet, a compact which comprises 70 to 90 wt % of a hard phase component consisting essentially of 50 to 80 wt % of Ti on a carbide, nitride or carbonitride basis and 10 to 40 wt % of an element of the Group VIa in the Periodic Table on a carbide basis and having an atomic ratio (nitrogen/carbon+nitrogen) of 0.4 to 0.6, and 10 to 30 wt % of a binder phase component consisting essentially of an iron group metal is put in a vacuum oven, and heated at a temperature higher than a liquidus temperature of the iron group metal while nitrogen gas is introduced therein at a pressure of 1 to 30 torr. After the oven reaches a maximum sintering temperature, the compact is baked at a reduced nitrogen gas pressure. Thus, a TiCN cermet is obtained which has a maximum case surface roughness of not greater than 3.5 μm and a porosity of not higher than A-1, and has a 1000-μm thick surface portion which has been modified to have a higher toughness and hardness than an inner portion thereof.

In the hard phase component of the TiCN cermet, Ti is present in a proportion of 50 to 80 wt %, particularly 55 to 65 wt % on a carbide, nitride or carbonitride basis, and the Group VIa element in the periodic table such as W or Mo is present in a proportion of 10 to 40 wt %, particularly 15 to 30 wt % on a carbide basis.

If the proportion of Ti in the hard phase component is smaller than 50 wt %, the abrasion resistance is reduced. If the proportion of Ti is greater than 80 wt %, the sinterability is disadvantageously reduced. The Group VIa element is generally effective to suppress the growth of grains and to improve wetability to the binder phase. If the proportion of the Group VIa element is smaller than 10 wt %, the aforesaid effects cannot be provided, so that the hard phase is roughened and the hardness and strength are reduced. If the proportion of the Group VIa element is greater than 40 wt %, the sintering becomes difficult with generation of an improper phase such as an η-phase.

In the hard phase component, Ta and Nb may additionally be present for improvement of the crater wear resistance, and nitrides, carbides and carbonitrides of Zr, V, Hf and the like may be present for improvement of resistance to plastic deformation in addition to the aforesaid elements in a total amount of 5 to 40 wt %. If the proportion is greater than 40 wt %, deterioration of the abrasion resistance and development of pores and voids are disadvantageously enhanced.

The binder phase essentially comprises an iron group metal such as Fe, Co or Ni, and may additionally comprise an element constituting the hard phase component.

In the sintered material, the hard phase component is present in a proportion of 70 to 90 wt % and the binder phase component is present in a proportion of 10 to 30 wt %.

The cermet to be used as a material for the base in the present invention is typically characterized in that the atomic ratio (nitrogen/carbon+nitrogen) in the hard phase component is in the range of 0.4 to 0.6, particularly 0.4 to 0.5. If the atomic ratio is smaller than 0.4, improvement in toughness and abrasion resistance cannot be expected. If the atomic ratio is greater than 0.6, pores and voids may be developed in the sintered material, thereby reducing the reliability of the throw-away tip.

The cermet is further characterized in that, though a great amount of nitrogen is incorporated therein, the surface of the sintered compact is very smooth with virtually no pore nor void and with a maximum surface roughness of not greater than 3.5 μm. Therefore, the throw-away tip composed of the cermet maintains improved toughness, abrasion resistance and heat resistance for an extended period and, hence, has a longer life and a higher reliability. In addition, there is no need to subject the sintered material to a polishing process, so that the sintered material can serve as a product on an "as is" basis.

For production of the TiCN cermet, a compact is first prepared which comprises 70 to 90 wt % of the hard phase component consisting essentially of 50 to 80 wt % of Ti on a carbide, nitride or carbonitride basis and 10 to 40 wt % of the Group VIa element in the periodic table on a carbide basis and having an atomic ratio (nitrogen/carbon+nitrogen) of 0.4 to 0.6, and 10 to 30 wt % of the binder phase.

More specifically, TiC, TiN and/or TiCN is used as a Ti-based powdery starting material, and WC, Mo2C and/or MoC, or a composite carbide or composite carbonitride thereof is used as a Group VIa element based material. These materials are blended to provide the aforesaid composition, and then molded into a compact by known molding means, e.g., press molding, extrusion molding, cast molding, injection molding or a cold isostatic molding.

As described above, carbides, nitrides and carbonitrides of Ta, Nb, Zr, V, Hf and the like may be added in combination. If TiC is used alone as the Ti-based material, the sinterability is reduced thereby to cause partial grain growth. Therefore, Ti(CN) is preferably used alone or in combination with TiN.

The resulting compact is put in a vacuum oven, and sintered.

More specifically, the compact is heated in a vacuum oven under a pressure of not higher than 0.5 torr, and 1- to 30-torr nitrogen gas is introduced into the vacuum oven at predetermined timing. The introduction of the nitrogen gas suppresses pyrolysis of the nitride such as TiN contained in the compact, thereby preventing development of pores and voids. The timing at which the nitrogen gas is introduced in the sintering process is particularly important. In general, the densification of the compact starts at a temperature around the liquidus temperature of the iron group metal in the course of the temperature rise. The nitrogen gas is introduced when the compact is densified by a theoretical density ratio of 5% or more with respect to the initial compact at a temperature not lower than the liquidus temperature. When the compact is densified by 5% or more, a liquidus film is formed on the surface of the compact. The introduction of the nitrogen gas after the formation of the liquidus film causes nitrogen gas to remain in interstices in the compact and, as a result, prevents the formation of pores and voids.

However, if the nitrogen gas is introduced when the theoretical density ratio exceeds 90%, the decomposition of the nitride cannot effectively be suppressed, so that the resulting sintered material is liable to have a roughened surface. Therefore, the introduction of the nitrogen gas is preferably started when the density ratio is lower than 90%.

After the temperature in the oven reaches the maximum sintering temperature, the pressure of the nitrogen gas is reduced lower than the previous level or to the vacuum, or gradually reduced for the sintering. This is because, if the pressure is further increased after the maximum sintering temperature is reached, a rough and brittle nitride layer containing little metal is formed on the surface of the sintered material, thereby resulting in roughening of the case surface and remarkable reduction of the toughness of the surface portion.

A reason why the nitrogen gas pressure is set at 1 to 30 torr is that a pressure of lower than 1 torr cannot effectively suppress the decomposition of the nitride and a pressure of greater than 30 torr reduces the sinterability and results in deposition of free carbon and reduction of the toughness of the sintered material.

Such a preparation method virtually eliminates the development of pores and voids in the sintered material to smooth the surface of the sintered material. Another characteristic feature of the preparation method of the present invention is that the very hard and tough modified surface layer is formed on the surface of the sintered material as described above.

Although a throw-away tip base of any of various shapes can be formed of the cermet, the contraction speed at the sintering is preferably controlled in accordance with the complexity of the shape of the base. This is because the compact contracts in accordance with a contraction curve which differs from part to part thereof and, if the complexity of the shape of the compact is increased, minute pores and cracks may occur on the surface of the finally obtained sintered material.

For prevention of such a phenomenon, it is necessary to reduce the contraction speed of the compact at the sintering.

In this respect, an inert gas such as He or Ar is preliminarily introduced at the introduction of the nitrogen gas to suppress the decomposition of the nitride and to allow the contraction of the compact to proceed moderately without deterioration of the sinterability. The inert gas is preferably introduced at a temperature lower by about 50 to 20 degrees than the nitrogen gas introduction temperature and at a pressure of not higher than 1 atm.

④ Cemented Carbide

A cemented carbide to be herein employed comprises a hard phase and a binder phase. The hard phase consists essentially of tungsten carbide, or tungsten carbide of 5 to 15 wt % of which is replaced with at least one of carbides, nitrides and carbonitrides of metals of the Group VIa, Va and VIa in the Periodic Table. Where a component other than tungsten carbide is blended, the hard phase comprises a WC phase and a solid solution phase of a composite carbide or a solid solution phase of a composite nitride. The binder phase consists essentially of an iron group metal such as Co, which is present in a proportion of 5 to 15 wt % based on the total binder phase.

A preferred cemented carbide comprises a phase consisting of cobalt tungsten carbide in addition to the hard phase and the binder phase. Examples of known cobalt tungsten carbide include $Co_3W_3C$, $Co_6W_6C$, $Co_2W_4C$ and $Co_3W_9C_4$. The highest peaks observed in X-ray diffraction patterns of these cobalt tungsten carbides are a (333) and (511) composite peak for $Co_3W_3C$, a (333) and (511) composite peak for $Co_6W_6C$, a (333) and (511) composite peak for $Co_2W_4C$ and a (301) peak for $Co_3W_9C_4$. It is important that a peak intensity ratio I1/I2 is greater than zero and not greater than 0.15, preferably 0.01 to 0.10, wherein I1 is the height of the highest intensity peak in the peaks of the cobalt tungsten carbides and I2 is the height of the highest peak, i.e., the height of a (001) peak of tungsten carbide WC. A reason why the peak intensity ratio is set within the aforesaid range is as follows. If the intensity ratio is zero, the cobalt tungsten carbides do not deposit in the cemented carbide, resulting in reduction of the abrasion resistance of the base. If the intensity ratio is greater than 0.15, the cobalt tungsten carbides excessively deposit, resulting in reduction of the hardness of the cemented carbide.

The cobalt tungsten carbide phase is preferably present as a phase having an average grain diameter of not greater than 5 μm, particularly not greater than 3 μm in the cemented carbide. If the average grain diameter is greater than 5 μm, the strength of the entire cemented carbide is reduced because the cobalt tungsten carbides are intrinsically brittle. Most preferably, the average grain diameter is not greater than 2 μm.

As the cobalt tungsten carbide phase is generated, W diffuses into the Co binder phase to form a solid solution therein, so that the lattice constant of Co changes. The lattice constant of Co in the cemented carbide is preferably in the range of 3.55 to 3.58.

For preparation of the cemented carbide, a powdery WC starting material, one or more powdery materials selected from the carbides, nitrides and carbonitrides of the metals of the Groups IVa, Va and VIa in the periodic table, and Co powder are respectively weighed in the aforesaid amounts, mixed together and milled. The resulting powder mixture is molded into a compact by a known molding method such as press molding, and the resulting compact is sintered.

The sintering is performed in vacum under a pressure of $10^{-1}$ to $10^{-3}$ torr in a temperature range between 1623 and 1773 K for 10 minutes to 2 hours. The deposition of the cobalt tungsten carbides is controlled by properly determining the total amount of carbon including the amount of carbon in the starting material and the amount of additional carbon powder, and the amount of the additional carbides, nitrides and carbonitrides of the metals of the Groups IVa, Va and VIa which are to be substituted for some of tungsten carbide. Where the amount of the carbon in the starting material to be used is lower than a stoichiometric amount, for example, the deposition easily occurs.

The deposition of a very small amount of the cobalt tungsten carbides in the cemented carbide makes it possible to impart an excellent cutting ability to the throw-away tip particularly for cutting stainless steel. The cobalt tungsten carbides per se are very hard and, therefore, excellent in abrasive resistance. Further, a reduced amount of carbon are diffused into the binder phase to form a solid solution and the amount of tungsten is correspondingly reduced as the cobalt tungsten carbides are generated, whereby the binder phase is strengthened. In addition, the generated cobalt tungsten carbides have different expansion coefficients from that of the WC phase occupying a major portion of the cemented carbide, so that residual compressive stress occurs therein to improve the chipping resistance.

(3) Conductive Film for the Sensor Lines and the Like

The sensor lines to be formed on the flanks of the base of the throw-away tip have a predetermined electrical resistance. A change in the electrical resistance is measured by means of an ohm meter to detect the abrasion and chipping of the throw-away tip.

Examples of a material for the sensor lines include: metallic materials including metals of the Groups IVa, Va and VIa such as Ti, Zr, V, Nb, Ta, Cr, Mo and W, iron group metals such as Co, Ni and Fe, and Al; carbides, nitrides and carbonitrides of the metals of the Groups IVa, Va and VIa such as TiC, VC, NbC, TaC, $Cr_3C_2$, $Mo_2C$, WC, $W_2C$, TiN, VN, NbN, TaN, CrN, TICN, VCN, NbCN, TaCN and CrCN; and (Ti,Al)N.

Among these materials, TiN is preferable for the following reasons. TiN has good adhesion to the base of the throw-away tip. TiN is nonreactive with a workpiece and the sensor lines of TiN constantly exhibit a predetermined electrical resistance, so that the abrasion and chipping of the throw-away tip can accurately be detected. TiN effectively prevents a work surface of a workpiece from being scratched by a reaction product thereof. TiN has an excellent acid resistance, so that the electrical resistance of the sensor lines is hardly changed by generation of an oxide. Therefore, the abrasion and chipping of the throw-away tip can accurately be detected.

The sensor lines are formed in the following manner. A conductive film of a predetermined thickness is formed on the flanks of the base of the throw-away tip by a CVD method, a PVD method such as ion plating, sputtering or evaporation, or a plating method. Thereafter, the conductive film is patterned into a predetermined configuration by laser machining or etching.

More specific methods for forming the sensor lines are as follows.

Where the sensor lines are formed of TiN by the CVD method, for example, the base of the throw-away tip is put in a reaction vessel of a heat resistant alloy which is condition at a temperature of 900° C. to 1050° C. and at a pressure of 10 to 100 kPa. Then, $TiCl_4$, $H_2$ and $N_2$ are introduced into the reaction vessel at flow rates of 1 to 5 ml/min, 20 to 30 l/min and 10 to 20 l/min, respectively, for 20 minutes to provide a reaction product of TiN and HCl, whereby the base of the throw-away tip is coated with TiN.

Where the sensor lines are formed of (Ti,Al)N or (Ti,Al)CN by ion plating which is one kind of the PVD method, for example, the base of the throw-away tip and a cathode electrode (target) of a Ti-Al alloy are placed in an arc ion plating apparatus. After the inside of the apparatus is heated up to 500° C. under vacuum at $1 \times 10^{-5}$ torr, Ar gas is introduced into the apparatus to create an Ar atmosphere of $1 \times 10^{-3}$ torr. Then, a bias voltage of −800 V is applied to the base in this state, whereby the surface of the base is subjected to gas bombard cleaning. Finally, nitrogen gas or nitrogen gas plus methane gas as a reaction gas is introduced into the apparatus to create a reaction atmosphere at $5 \times 10^{-3}$ torr, and the bias voltage applied to the base is reduced to −200 V to cause arc discharge between the cathode electrode and an anode electrode. The Ti-Al alloy freed from the cathode electrode is allowed to react in the reaction atmosphere, whereby the base is coated with (Ti,Al)N or (Ti,Al)CN.

The conductive film of TiN, (Ti,Al)N, (Ti,Al)CN or the like formed on the surface of the base of the throw-away tip is patterned into a predetermined configuration for formation of the sensor lines, the contact regions, the connection lines and the like by laser machining or etching. Where the laser machining is employed for the patterning, for example, a YAG laser beam having a width of 50 μm, a wavelength of 1.06 μm and an output of 35 kHz and 10 A is scanned over the TiN film or the like formed on the surface of the base at a drawing speed of 100 to 300 mm/s. Alternatively, a $Co_2$ laser having an illumination spot diameter of 0.3 mm and an output of 20 W is scanned over the TiN film at a drawing speed of 0.3 m/min.

If the conductive film is thin with a thickness of less than 0.05 μm, the adhesion of the conductive film to the surface of the base is poor and the electrical resistance of the sensor line is increased, so that it may be difficult to accurately detect the abrasion and chipping of the throw-away tip. If a conductive film having a thickness of greater than 20 μm is to be formed, a great internal stress occurs inside the conductive film at the formation thereof, whereby the conductive film may have poor adhesion to the surface of the base. Therefore, the thickness of the conductive film is preferably in the range of 0.05 to 20 μm, most preferably 0.1 to 5 μm.

Where the base of the throw-away tip is composed of an insulative material such as a sintered alumina based material, a sintered silicon nitride based material or cBN, the sensor lines and the like are formed directly on the surface of the base. Where the base is composed of a conductive material such as a cemented carbide or a cermet, an intermediate layer of an insulative material such as alumina intervenes between the sensor lines and the base.

The intermediate layer of an insulative material such as alumina serves for electrical isolation of the sensor lines and the like. The intermediate layer which has a predetermined thickness is formed between the surface of the base and the sensor lines and the like (conductive film) by a CVD method or the like.

More specifically, where the intermediate layer is composed of alumina, the formation of the intermediate layer is achieved in the following manner. The base of the throw-away tip is placed in a reaction vessel of a heat resistant alloy which is condition at a temperature of about 1050° C. and at a pressure of 6.5 kPa. Then, $H_2$, $CO_2$ and $AlCl_3$ are introduced into the reaction vessel at flow rates of 40 to 50 l/min, 1 to 3 l/min and 0.5 to 2 l/min, respectively, for two hours to generate $Al_2O_3$, whereby the base is coated with $Al_2O_3$.

If the intermediate layer has a thickness of less than 1 μm, electrical short may occur between the base and the sensor lines, so that the abrasion and chipping of the throw-away tip cannot accurately be detected. If an intermediate layer having a thickness of greater than 10 μm is to be formed, a great internal stress occurs inside the intermediate layer at the formation thereof, whereby the intermediate layer may have poor adhesion to the surface of the base. Even with application of a small external force, the intermediate layer may readily be separated from the surface of the base. Therefore, the thickness of the intermediate layer is preferably in the range of 1 μm to 10 μm.

Next, examples of the throw-away tip with the abrasion sensor according to the present invention will be described which are adapted for detection of abrasion.

EXAMPLE 1

A base of a throw-away tip was formed of a sintered alumina based material, and sensor lines were formed of a conductive film of TiN in a configuration as shown in FIG. 1 on the base. The sensor line had a thickness of 0.3 μm and a width of 0.186 mm. The throw-away tip with the abrasion sensor was attached to the holder shown in FIG. 5. Then, a round rod workpiece of SCM435 (chromium molybdenum steel) was sequentially cut under the following machining conditions on an NC machine tool, while the resistance of the sensor line was measured. The result is shown in FIG. 7.

| Machining conditions: | |
|---|---|
| Cutting speed | V = 200 m/min |
| Cutting depth | d = 2 mm |
| Feed | f = 0.2 mm/rev |
| Wet machining | |
| Workpiece | Round rod of SCM435 (chromium molybdenum steel) |

Figure 7:
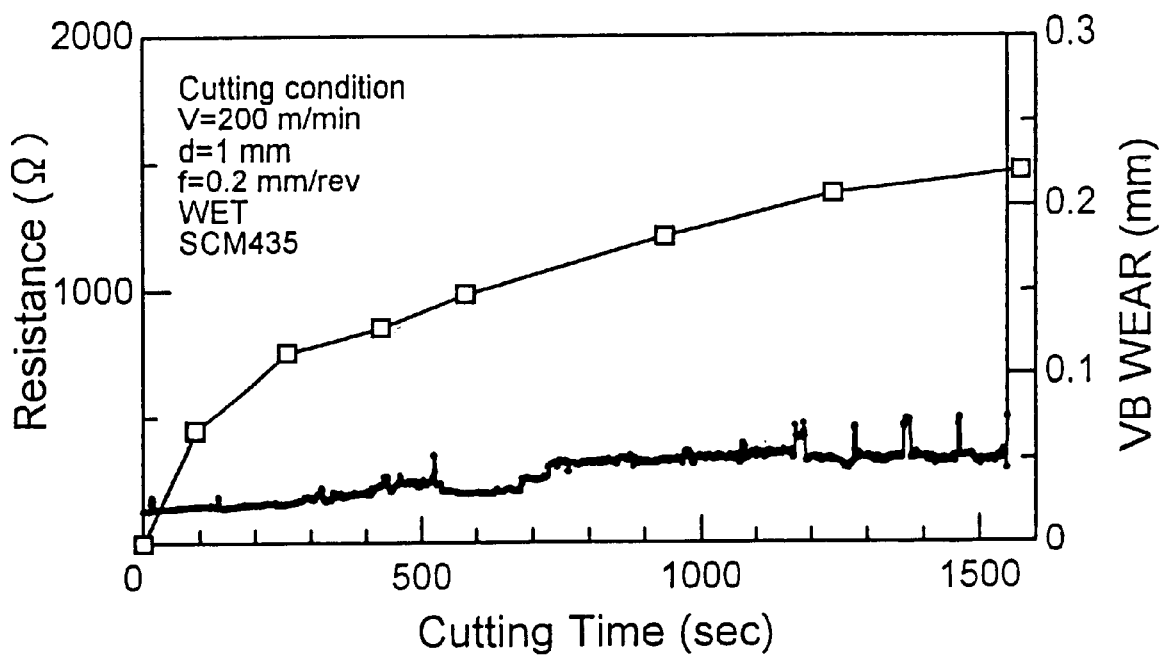
FIG. 7 is a graph showing the results of a test performed in Example 1.

In FIG. 7, a jaggy line graph illustrates changes in the resistance thus measured, wherein the resistance and the time are plotted as the ordinate and the abscissa, respectively. The graph shows that the resistance steeply increased after the lapse of 16.6 minutes from the start of the machining. For reference, the abraded states (abrasion widths) of the cutting edge were measured after the lapse of 11 minutes and 18 minutes from the start of the machining, and plotted to form a line graph, which shows a change in the abrasion width at a cutting front over time.

This measurement shows that, when the resistance steeply increased after the lapse of 16.6 minutes from the start of the machining, the abrasion reached the sensor film width (0.186 mm). Thus, a time point at which the abrasion reached the allowable abrasion limit can definitely be detected.

EXAMPLE 2

Figure 8:
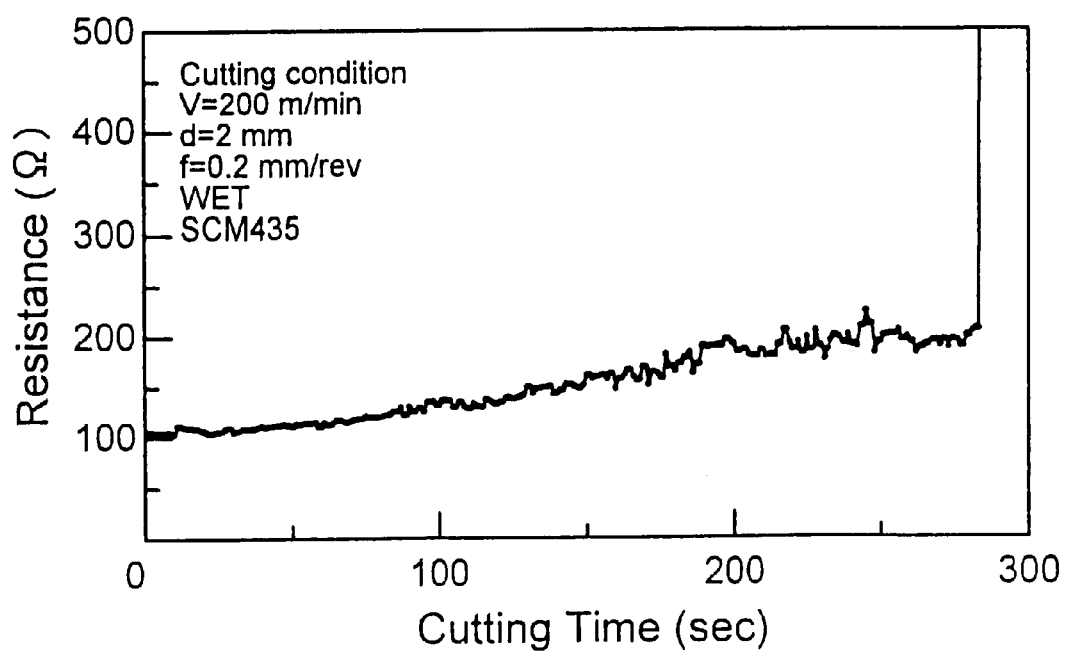
FIG. 8 is a graph showing the results of a test performed in Example 2.

A throw-away tip as employed in Example 1 was attached to the holder shown in FIG. 5. Then, a round rod workpiece of SCM435 (chromium Molybdenum steel) having four grooves was sequentially cut under the following conditions on an NC machine tool, while the resistance of a sensor line was measured. The result is shown in FIG. 8.

| Machining conditions: | |
|---|---|
| Cutting speed | V = 200 m/min |
| Cutting depth | d = 2 mm |
| Feed | f = 0.2 mm/rev |
| Wet machining | |
| Workpiece | Round rod of SCM435 (chromium molybdenum steel) with four grooves |

After the lapse of 40 odd seconds, the resistance steeply increased to infinity. The machining was interrupted to check a cutting ridge of the throw-away tip, and it was found that the cutting ridge was chipped. This experiment shows that, when the cutting ridge was chipped to be unusable, the sensor line was cut off. As a result, the chipping of the cutting ridge of the throw-away tip can definitely be detected on the basis of the abnormal change in the resistance thus measured.

EXAMPLE 3

Figure 9:
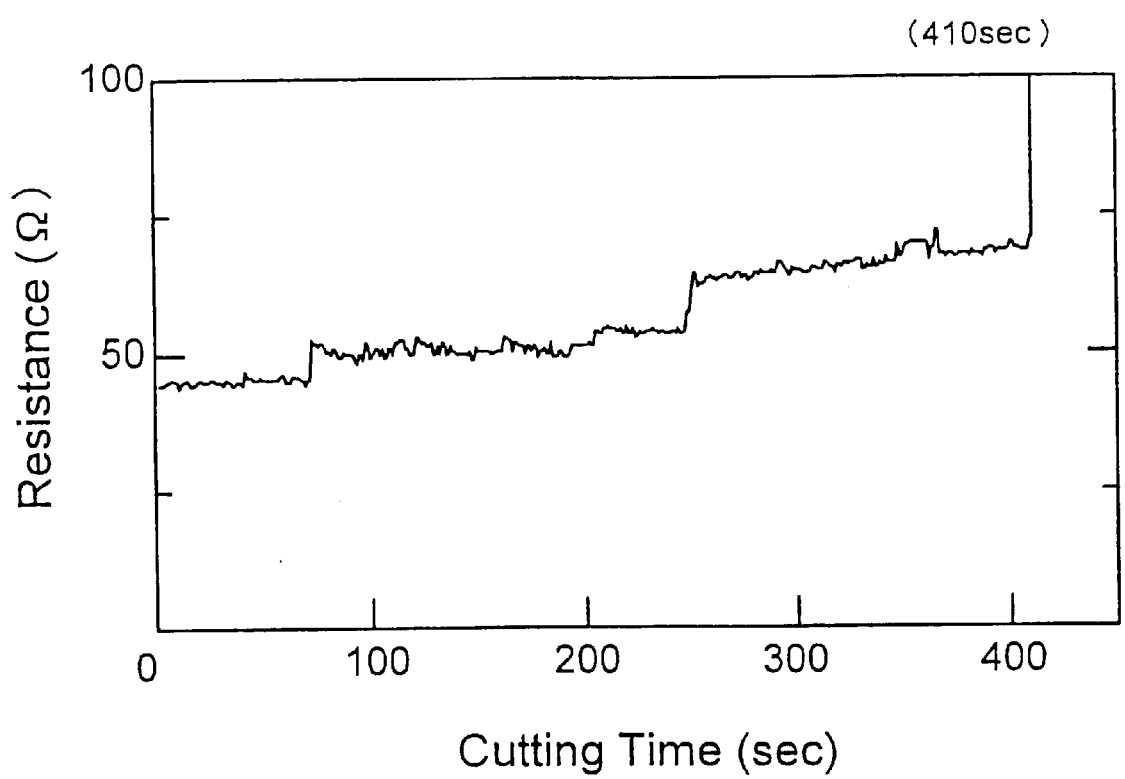
FIG. 9 is a graph showing the results of a test performed in Example 3.

A base of a throw-away tip was formed of a sintered silicon nitride based material, and three parallel sensor lines were formed of a conductive film of TiN in a configuration as shown in FIG. 4 on the base. The sensor lines each had a thickness of 0.3 μm and a width of 0.146 mm. Each adjacent pair of sensor lines were spaced 0.01 mm. The throw-away tip with the abrasion sensor was attached to the holder shown in FIG. 5. Then, a round rod workpiece of FC250 (gray cast iron) was sequentially cut under the following machining conditions on an NC machine tool, while the resistance of the sensor lines was measured. The result is shown in FIG. 9.

| Machining conditions: | |
|---|---|
| Cutting speed | V = 200 m/min |
| Cutting depth | d = 2 mm |
| Feed | f = 0.2 mm/rev |
| Wet machining | |
| Workpiece | Round rod of FC250 (gray cast iron) |

The measured resistance increased stepwise over the machining time, and finally reached infinity. As the abrasion of the tip proceeded, the respective sensor lines were successively cut off, whereby the resistance increased stepwise. When the third sensor line was cut off (after the lapse of about 10 minutes), the resistance increased to infinity. Thus, a time point at which all the sensor lines were worn out and the cutting edge of the throw-away tip reached the allowable abrasion limit can be detected.

While the present invention has thus been described in detail by way of the specific embodiments thereof, it should be understood that the invention be not limited to the embodiments, but various modifications may be made within the scope of the invention defined by the following claims.

What is claimed is:

1. A throw-away tip with an abrasion sensor comprising:
 a generally planar base, one surface of the base defining a rake face, side faces of the base that intersect the rake face defining one or more flanks and one or more restricted faces, the one or more restricted faces being adapted to be fixed in abutment against a restriction face of a holder when the throw-away tip is mounted in the holder;
 a cutting ridge defined by an intersection between the rake face and at least one flank;
 a sensor line of a conductive film provided along the cutting ridge on the at least one flank in an electrically insulative relation with respect to the base;
 a contact region provided on at least one restricted face in an electrically insulative relation with respect to the base, the contact region being electrically connectable to an external circuit; and
 a connection portion provided on the base in an electrically insulative relation with respect to the base and connecting the contact region to an end of the sensor line.

2. A throw-away tip with an abrasion sensor as set forth in claim 1,
 wherein the side faces of the base that intersect the rake face further define two or more flanks, at least two of the flanks being adjacent,
 wherein a cutting nose portion is defined by an intersection between the rake face and two adjacent flanks,
 wherein the sensor line extends along the cutting ridge as surrounding the nose portion;
 wherein the contact region includes a pair of contact regions, wherein the connection portion comprises a connection line provided on the flank to connect one of the contact regions on the restricted face to one of opposite ends of the sensor line, and a connection region provided on the rake face to connect the other contact region on the restricted face to the other end of the sensor line.

3. A throw-away tip with an abrasion sensor as set forth in claim 2,
 wherein the base has a generally square plan shape and the side faces of the base that intersect the rake face further define two restricted faces defined by two side faces opposite from the respective flanks,
 wherein one contact region is provided on one of the restricted faces and the other contact region is provided on the other restricted face.

4. A throw-away tip with an abrasion sensor as set forth in claim 2,
 wherein the base has a generally square plan shape and the side faces of the base that intersect the rake face further define two restricted faces defined by two side faces opposite from the respective flanks,
 wherein the pair of contact regions are juxtaposed on one of the restricted faces.

5. A throw-away tip with an abrasion sensor as set forth in claim 2,
 wherein the nose portion includes a plurality of nose portions,
 wherein a plurality of sensor lines are provided for the respective nose portions, and a plurality of connection portions and plural pairs of contact regions connected to the respective sensor lines are provided for the respective nose portions,
 wherein conduction paths including the sensor lines, the connection portions and the contact regions are arranged in the same pattern.

6. A throw-away tip with an abrasion sensor as set forth in claim 3,
 wherein the nose portion includes a plurality of nose portions,
 wherein a plurality of sensor lines are provided for the respective nose portions, and a plurality of connection portions and plural pairs of contact regions connected to the respective sensor lines are provided for the respective nose portions, wherein conduction paths including the sensor lines, the connection portions and the contact regions are arranged in the same pattern.

7. A throw-away tip with an abrasion sensor as set forth in claim 4, wherein the nose portion includes a plurality of nose portions, wherein a plurality of sensor lines are provided for the respective nose portions, and a plurality of connection portions and plural pairs of contact regions connected to the respective sensor lines are provided for the respective nose portions, wherein conduction paths including the sensor lines, the connection portions and the contact regions are arranged in the same pattern.

8. The throw-away tip with an abrasion sensor as set forth in claim 1, wherein the sensor line has a width less than or equal to an allowable abrasion limit of the cutting ridge.

9. The throw-away tip with an abrasion sensor as set forth in any of claims 2 to 7, wherein the sensor line has a width less than or equal to an allowable abrasion limit of the cutting nose portion.

\* \* \* \* \*